United States Patent
Tsuji et al.

(10) Patent No.: US 8,481,764 B2
(45) Date of Patent: Jul. 9, 2013

(54) PROCESS FOR PRODUCING PROPYLENE OXIDE

(75) Inventors: Junpei Tsuji, Chiba (JP); Koji Shinohara, Chiba (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 518 days.

(21) Appl. No.: 11/997,965

(22) PCT Filed: Aug. 22, 2006

(86) PCT No.: PCT/JP2006/316791
§ 371 (c)(1),
(2), (4) Date: Feb. 27, 2008

(87) PCT Pub. No.: WO2007/023977
PCT Pub. Date: Mar. 1, 2007

(65) Prior Publication Data
US 2010/0145081 A1 Jun. 10, 2010

(30) Foreign Application Priority Data
Aug. 25, 2005 (JP) ................................. 2005-244050

(51) Int. Cl.
*C07D 301/19* (2006.01)
*C07D 301/12* (2006.01)
*C07D 301/06* (2006.01)

(52) U.S. Cl.
USPC ............ 549/533; 549/529; 549/531; 549/532

(58) Field of Classification Search
USPC ........................ 549/529, 531, 532, 533, 534
See application file for complete search history.

(56) References Cited

U.S. PATENT DOCUMENTS

| 3,518,285 | A | * | 6/1970 | Wolgemuth et al. | 549/531 |
| 5,723,637 | A | * | 3/1998 | Tsuji et al. | 549/529 |
| 6,172,244 | B1 | | 1/2001 | Heisel | |
| 2003/0032823 | A1 | | 2/2003 | Tsuji et al. | |
| 2004/0127729 | A1 | | 7/2004 | Oku et al. | |
| 2005/0082159 | A1 | | 4/2005 | Oku et al. | |
| 2009/0209771 | A1 | | 8/2009 | Tsuji et al. | |

FOREIGN PATENT DOCUMENTS

| CN | 1432005 A | 7/2003 |
| CN | 1525965 A | 9/2004 |
| CN | 1633422 A | 6/2005 |
| EP | 0 345 856 A1 | 12/1989 |
| EP | 6 23389 A1 | 11/1994 |
| EP | 1 266 890 A1 | 12/2002 |
| EP | 1 837 334 A1 | 9/2007 |
| JP | 2003-327576 A | 11/2003 |
| JP | 2005-97208 A | 4/2005 |
| JP | 2006-232744 A | 9/2006 |
| WO | WO 99/32472 A1 | 7/1999 |
| WO | WO 03/050100 A1 | 6/2003 |
| WO | 2006/075777 A1 | 7/2006 |

* cited by examiner

*Primary Examiner* — Taylor Victor Oh
(74) *Attorney, Agent, or Firm* — Sughrue Mion, PLLC

(57) ABSTRACT

A process for producing propylene oxide, which comprises supplying an organic peroxide and propylene to an epoxidation reactor in which a solid catalyst is packed thereby continuously producing propylene oxide through epoxidation reaction, wherein said process comprises cooling at least a part of the propylene before supplying to separate and remove water contained in the propylene, and supplying the propylene in which water has been separated and removed to the epoxidation reactor.

5 Claims, No Drawings

PROCESS FOR PRODUCING PROPYLENE OXIDE

TECHNICAL FIELD

The present invention relates to a process for producing propylene oxide.

BACKGROUND ART

For example, it is publicly known to continuously produce propylene oxide through epoxidation reaction by supplying an organic peroxide and propylene to an epoxidation reactor in which a solid catalyst such as titanium-containing silicon oxide is packed (e.g. EP 0345856 A). However, there were problems that a pressure loss of a solid catalyst layer increased with a continuous operation time and the catalyst was destroyed when the pressure loss was over the pressure resistant strength of the catalyst, and that the production amount had to be decreased through suppression of the amount to be supplied of the raw material for avoiding the destroy of the catalyst.

DISCLOSURE OF THE INVENTION

Under such situations, an object of the invention is to provide a process for continuously producing propylene oxide through epoxidation reaction by supplying an organic peroxide and propylene to an epoxidation reactor in which a solid catalyst is packed, the process being able to avoid the destroy of the solid catalyst generated by increase of a pressure loss of the catalyst layer and the situation that reduction of the production amount is forced.

Namely, the present invention relates to a process for producing propylene oxide, which comprises supplying an organic peroxide and propylene to an epoxidation reactor in which a solid catalyst is packed thereby continuously producing propylene oxide through epoxidation reaction, wherein said process comprises cooling at least a part of the propylene thereby separating and removing water contained in the propylene, and subsequently supplying the propylene to the epoxidation reactor.

BEST MODE FOR CARRYING OUT THE INVENTION

In the present invention, propylene oxide is continuously produced through epoxidation reaction by supplying an organic peroxide and propylene to an epoxidation reactor in which a solid catalyst is packed As a solid epoxidation catalyst, titanium-containing silicon oxide is used from the viewpoint of obtaining propylene oxide under high yield. As the catalyst, so-called Ti-silica catalysts containing titanium chemically bonded to silicon oxide, are preferable. For example, a catalyst prepared by supporting a Ti compound on a silica carrier, a catalyst prepared by combining a titanium compound with silicon oxide by a co-precipitation method or sol-gel method, zeolite compounds containing Ti, and the like, can be listed.

Specific examples of the present invention include a process for continuously producing propylene oxide through epoxidation reaction by supplying an organic peroxide to a fixed bed reactor in which a titanium-containing silicon oxide catalyst is packed.

Examples of the organic peroxide include cumene hydroperoxide, ethylbenzene hydroperoxide and tert-butyl hydroperoxide. The organic peroxide to be supplied to the epoxidation reactor can be synthesized by oxidation of a hydrocarbon corresponding to the peroxide. An organic acid generated in the oxidation, decreases the yield of epoxidation. Therefore, from viewpoints of removal of the organic acid, it is preferable to contact the organic peroxide to be supplied to the epoxidation reactor with an aqueous solution of an alkali metal compound during and/or after the oxidation. As the compound containing the alkali metal, sodium hydroxide, sodium carbonate, potassium hydroxide, potassium carbonate and the like are listed. Further, an aqueous solution of anyone of these compounds or a mixture thereof can be used. The concentration of the alkali metal of the aqueous solution is preferably 0.05 to 10% by weight.

When the concentration is lower than 0.05% by weight, the removal of the organic acid may become insufficient, and, on the other hand, when the concentration is higher than 10% by weight, the yield of the organic peroxide may be reduced by which decomposition of the formed organic peroxide is promoted. After contact with the aqueous solution containing the alkali metal compound, the resulting mixture is separated into an oil phase and an aqueous phase, the oil phase is contacted with water for removing the alkali metal compound remained in the oil phase, and then the resulted mixture is separated into an oil phase and an aqueous phase. These operations may be repeated if necessary.

The oil phase separated often contains a traced amount of water. This water is preferably removed as much as possible because the water also deteriorates the yield of epoxidation. Methods for removing water include publicly known methods such as a removing method using a separation membrane such as a corelesser, a method for removing by consuming water through a reaction, and a method for removing water by means of distillation. From the industrial viewpoint, it is preferable to remove water by means of distillation. A solution containing the organic peroxide thus obtained is supplied to the epoxidation reactor.

The epoxidation reaction is carried out in a liquid phase using a solvent. The solvent should be liquid under a temperature and a pressure during the reaction, and substantially inert to reactants and products. The solvent may be a substance present in a hydroperoxide solution to be used. For example, when cumene hydroperoxide is a mixture with cumene which is a raw material thereof, the cumene can be used as a substitute of a solvent without particularly adding a solvent. The epoxidation temperature is usually from 0 to 200° C., and preferably from 25 to 200° C. The pressure may be a pressure sufficient to keep the reaction mixture in a liquid condition. In general, the pressure is advantageously from 0.1 to 10 MPa.

A molar ratio of propylene to the organic peroxide compound to be supplied to the epoxidation reactor is preferably 2/1 to 50/1. When the ratio is lower than 2/1, the efficiency may be low because the reaction velocity decreases. In contrast, when the ratio is over 50/1, large energy may be required in a step for separating and recovering propylene from a reaction mixture obtained in the epoxidation step for recycling excess amount of unreacted propylene.

In general, a liquid linear velocity of the reaction mixture in the continuous method using a fixed bed reactor, is preferably properly determined in the range of 0.1 to 3 cm/sec since the appropriate velocity varies depending on conditions such as a composition of the mixture and a particle size of the solid catalyst.

The unreacted propylene contained in the reaction mixture after the epoxidation reaction, is recycled to the epoxidation reactor after separation and recovery. As a method for the separation and recovery of unreacted propylene, distillation can be used. In the distillation, it is preferable to use conditions under which propylene is easily evaporated. Though the conditions of distillation vary depending on the temperature and composition of the reaction mixture supplied to a distillation step, the pressure is usually 0 to 5 and preferably 0 to 3 MPa as a gauge pressure, the overhead temperature is usually −50 to 150° C., and the bottom temperature is usually 50 to 200° C., and preferably 80 to 200° C.

Further, a method for distilling propylene stepwise using a plurality of distillation columns, may be used.

Unreacted propylene thus separated and recovered can be supplied to the epoxidation reactor after mixing with fresh propylene.

However, in a case of which propylene to be supplied to the epoxidation reactor contains unreacted propylene after epoxidation reaction, a problem that a pressure loss of the solid catalyst layer increases with an operation time, occurs.

In usual, oxygen-containing organic compounds as impurities are contained in the unreacted propylene. The oxygen-containing organic compounds are generated mainly in the epoxidation reactor. Examples of the oxygen-containing organic compounds include formaldehyde, acetaldehyde, formic acid and methyl alcohol. These oxygen-containing organic compounds are contained in the unreacted propylene separated and recovered from the reaction mixture after epoxidation, and supplied to the epoxidation reactor with recycling of the unreacted propylene thereto. However, these oxygen-containing organic compounds cause to an increase of the pressure loss during a long time continuous operation.

From facts that deposition of polymerized products of aldehydes on the solid catalyst in which the pressure loss increased, is significant, it is preferable to reduce the concentration of the aldehydes in propylene to be supplied to the epoxidation reactor.

In the present invention, the before-mentioned object can be attained by cooling at least part of propylene to be supplied to an epoxidation reactor thereby separating and removing water contained in the propylene, then supplying the propylene in which oxygen-containing organic compounds has been removed, to the epoxidation reactor.

Specific example of a cooling method of propylene is as follows: Usually, the unreacted propylene contains water generated in the epoxidation step, and the contained water is separated by cooling the propylene.

Propylene to be cooled may be unreacted propylene alone or a mixture of the unreacted propylene with propylene newly supplied. When the mixture with propylene newly supplied is cooled, this method is preferable since an amount of a cooling medium required for cooling can be reduced by mixing with propylene newly supplied lower in temperature than the unreacted propylene.

Water of about 0.01 to about 0.5% by weight is usually contained in propylene to be subjected to cooling.

As a cooling method, cooling with a heat exchanger, cooling by mixing with a fluent of low temperature, and cooling by a latent heat obtained through vaporization of a liquefied gas or the like are exemplified, and cooling with a heat exchanger is generally used industrially.

Though propylene to be cooled may be gas or liquid, it is required to be liquid in a step of separating generated water from propylene. As a specific example, gaseous propylene distilled from the overhead of a distillation column is cooled by a heat exchanger to liquefy it, an aqueous phase is separated at this time is separated. If necessary, liquefied propylene is further cooled to generate the aqueous phase and then separate it.

The temperature of propylene after cooled is usually −10 to 100° C., preferably 0 to 50° C. Therefore, the operation of a distillation column for recovery of unreacted propylene, should be conducted so that a overhead temperature of the column is higher than a temperature of propylene after cooled. When the cooled temperature is too low, the aqueous phase separated freezes to cause a trouble against a stable operation, and further it is required to use additional equipment such as a heat exchanger because energy for heating propylene at the time of supply of the propylene to the epoxidation step, becomes necessary, therefore, it leads to uneconomical.

In contrast, the temperature is too high, the separation of the aqueous phase becomes insufficient, therefore, it is not preferable from the viewpoint of separation of oxygen containing organic compounds. Moreover, the pressure added at cooling is not particularly restricted if the pressure is a pressure under which the propylene shows liquid at a cooling temperature.

The aqueous phase separated may be discarded through removal to the outside the system, or if necessary, reused in another step or another process. The water content in propylene after elimination of water is not particularly limited, but is preferably 300 ppm by weight or less, more preferably 100 ppm by weight or less.

The concentration of oxygen-containing organic compounds in propylene to be supplied to the epoxidation reactor is also reduced by removing the aqueous phase separated outside the system since the oxygen-containing organic compounds are dissolved in the aqueous phase separated.

As, in propylene to be subjected to cooling, the oxygen-containing organic compounds of 0.01 to 0.1% by weight is usually contained, aldehydes contained in propylene to be supplied to the epoxidation reactor is reduced to 100 ppm by weight or less, more preferably 50 ppm by weight or less. According to the above-described method, not only removal of water but also removal of water soluble aldehydes such as formaldehyde and acetaldehyde are possible.

Furthermore, as an effective removing method of oxygen-containing compounds in propylene to be supplied to the epoxidation reactor, it is possible to wash propylene with water, then to separate an aqueous phase for separation.

Specific examples of water washing of propylene are as follows:

As a washing method, there are given a method of contacting gaseous propylene with liquid-like or gaseous water, liquid propylene with liquid-like water or the like. It is preferable to contact liquid propylene with water in liquid form taking account of that propylene supplied to the epoxidation reactor is usually liquid, the contact efficiency and the volume required for contact. The liquid propylene is washed by contacting with water in liquid form in a part or whole of the propylene prior to supply to the epoxidation reactor. As an example of a method of contacting propylene with water, a method of contacting through mixing of them in a pipeline by simply injecting water into the pipeline of propylene, or a method of using a mixer or the like for improvement of contact efficiency can be applied.

As examples of the mixer, an agitation mixer composed of agitation means and container, can be listed, and if sufficient contact efficiency can be attained, a pipeline scaled mixer such as a static mixer can be used.

As contact conditions, any conditions can be used if sufficient washing is attained, and as preferable examples, the weight ratio of propylene to water of 0.1 to 200, the contact temperature of 4 to 120° C., and contact time of 1 to 1,800 seconds (excluding still standing time for separation) are illustrated. Propylene mixed with water is separated into an oil phase and an aqueous phase through still standing. As preferable conditions of still standing for separation, a still standing time for separation of 1 to 300 minutes and a still standing temperature of 4 to 120° C. are illustrated. The aqueous phase separated is discarded outside the system because the separated aqueous phase contains the oxygen-containing organic compounds, or, if possible, reused in another step or another process.

Further, a part thereof may be recycled and used for washing of propylene again.

As mentioned above, the increase of the pressure loss of the solid catalyst layer can be suppressed by supplying propylene in which water is separated and removed after the water washing, to the epoxidation reactor.

As above-mentioned, according to the present invention, propylene oxide can be efficiently produced from an organic peroxide and propylene.

The present invention is described in detail below.

EXAMPLE

Example 1

A titanium-containing silicon oxide catalyst prepared according to Example 1 of WO2004/056476 A was sieved to obtain the catalyst of 1 to 2 mm in particle size. Thus obtained catalyst was packed to a tubular epoxidation reactor made of SUS having an inner diameter of 2.5 cm, in which an inner tube having an outer diameter of 1 cm was concentrically placed to form a solid catalyst layer of about 140 cm in length.

To the reactor, an organic hydroperoxide and propylene shown below were continuously fed at a weight ratio of the organic hydroperoxide to propylene of 1:1 and a flow rate of 10 kg/hr to carry out epoxidation reaction in the catalyst layer. The reaction pressure of the outlet side of the reactor was 5.4 MPaG (gauge pressure). Further, during the reaction, the pressure difference between the inlet side and outlet side of the reactor (pressure loss) was measured. Though the reaction was continuously carried out for about 350 hours, the pressure loss and an increase of the pressure loss during the reaction were scarcely observed.

Organic Hydroperoxide:

As the organic hydroperoxide, a cumene solution containing 25% by weight of cumene hydroperoxide obtained by separating an oxidation liquid obtained by (1) oxidizing cumene with air in the presence of an aqueous sodium carbonate solution into an aqueous phase and an oil phase, (2) after contacting and mixing thus obtained oil phase with water, separating again into an aqueous phase and an oil phase, and further (3) removing water in a trace amount remained in the oil phase obtained in (2) through distillation, was used.

Propylene:

As propylene, propylene obtained by adding fresh purified propylene in an amount corresponding to the amount consumed by the epoxidation reaction to propylene obtained by cooling the unreacted propylene of 100° C. recovered by distillation of the reaction mixture to 20° C. thereby separating and removing water from the propylene, was used. In addition, the water separated and removed, contained 14% by weight of formaldehyde.

INDUSTRIAL APPLICABILITY

According to the present invention, there can be provided a process for continuously producing propylene oxide through epoxidation reaction by supplying an organic peroxide and propylene to an epoxidation reactor in which a solid catalyst is packed, which can avoid a destroy of the solid catalyst generated by increase of a pressure loss of the catalyst layer and a situation that reduction of the production amount is forced.

The invention claimed is:

1. A process for producing propylene oxide, which comprises supplying an organic hydroperoxide and propylene to an epoxidation reactor in which a solid catalyst is packed thereby continuously producing propylene oxide through epoxidation reaction, wherein said process comprises cooling at least a part of the propylene before supplying to separate and remove water contained in the propylene, and supplying the propylene in which water has been separated and removed to the epoxidation reactor, wherein the propylene to be subjected to cooling contains unreacted propylene recovered from a reaction mixture obtained after the epoxidation reaction, and the propylene to be subjected to cooling contains water and an aldehyde, wherein at least a part of the aldehyde is removed by being contained in water, the concentration of the aldehyde after separating and removing the water, is 100 ppm by weight or less, and the aldehyde is formaldehyde and/or acetaldehyde; and the solid catalyst is a titanium-containing silicon oxide catalyst.

2. The process according to claim 1, wherein the propylene to be subjected to cooling contains 0.01 to 0.5% by weight of water.

3. The process according to claim 1, wherein the propylene to be subjected to cooling contains 0.01 to 0.1% by weight of aldehyde.

4. The process according to claim 1, wherein the organic hydroperoxide to be supplied is a-one obtained by contacting with an alkali metal-containing aqueous solution.

5. The process according to claim 1, wherein the propylene is washed by water prior to cooling.

* * * * *